(12) United States Patent
Koslow

(10) Patent No.: US 6,485,813 B1
(45) Date of Patent: Nov. 26, 2002

(54) METHOD OF STABILIZING COMPOSITE MEDIA AND MEDIA PRODUCED THEREBY

(75) Inventor: Evan Koslow, Weston, CT (US)

(73) Assignee: Koslow Technologies Corp., Orange, CT (US)

(*) Notice: Subject to any disclaimer, the term of this patent is extended or adjusted under 35 U.S.C. 154(b) by 0 days.

(21) Appl. No.: 09/579,205

(22) Filed: May 26, 2000

Related U.S. Application Data

(60) Continuation-in-part of application No. 08/903,395, filed on Jul. 22, 1997, now Pat. No. 6,077,588, which is a division of application No. 08/813,055, filed on Mar. 7, 1997, now Pat. No. 5,792,513.

(51) Int. Cl.[7] .............................. B32B 5/16; B32B 5/18; B32B 5/22; B32B 5/30; B32B 7/14
(52) U.S. Cl. .................. 428/198; 428/212; 428/220; 428/327; 428/328; 428/329; 428/330; 428/331; 604/367; 604/368; 604/369; 604/370; 604/372; 604/378; 604/385.1
(58) Field of Search ............................ 428/220, 323, 428/327, 328, 329, 330, 332, 114, 198, 212, 331; 604/358, 365, 366, 367, 368, 369, 370, 372, 374, 378, 385.1

(56) References Cited

U.S. PATENT DOCUMENTS

| | | | |
|---|---|---|---|
| 2,865,800 A | 12/1958 | Stastny | 428/313.5 |
| 3,158,532 A | 11/1964 | Pall et al. | 210/505 |
| 3,238,056 A | 3/1966 | Pall et al. | 428/338 |
| 3,246,767 A | 4/1966 | Pall et al. | 210/505 |
| 3,325,341 A | 6/1967 | Shannon | 428/406 |
| 3,375,933 A | 4/1968 | Rodman | 210/502 |
| 3,538,020 A | 11/1970 | Heskett et al. | 264/122 |
| 3,573,158 A | 3/1971 | Pall et al. | 162/131 |
| T886,010 I4 | 5/1971 | Craven et al. | 442/374 |
| 3,592,767 A | 7/1971 | Pall et al. | 210/490 |
| 3,608,010 A | 9/1971 | Stayner | 521/135 |
| 3,726,755 A | 4/1973 | Shannon | 428/313.5 |
| 3,796,778 A | 3/1974 | Gallacher | 264/49 |
| 3,864,124 A | 2/1975 | Breton et al. | 75/212 |
| 3,919,369 A | 11/1975 | Holden | 264/45.1 |
| 3,986,851 A | 10/1976 | Grode | 55/488 |
| 4,055,184 A | 10/1977 | Karami | 604/359 |
| 4,061,807 A | 12/1977 | Shaler et al. | 428/71 |
| 4,180,211 A | 12/1979 | Olcott | 428/313.3 |
| 4,194,040 A | 3/1980 | Breton et al. | 428/422 |
| 4,200,679 A | 4/1980 | Klein | 428/402 |
| 4,222,977 A | 9/1980 | Dobo | 264/63 |
| 4,239,516 A | 12/1980 | Klein | 55/389 |
| 4,311,609 A | 1/1982 | Wagner et al. | 252/179 |

(List continued on next page.)

FOREIGN PATENT DOCUMENTS

| | | |
|---|---|---|
| EP | 0056724 | 7/1982 |
| WO | WO 94/01069 | 1/1994 |

OTHER PUBLICATIONS

Microthene®F Microfine Polyolefin Powders, U.S.I. Chemicals booklet, ©1980 (19 Pages).
Technical Data on Hovoglas® Laminated Filter Media LL–5211 A–A by Hollingsworth & Vose Company (2 pages).
Technical Data on Hovoglas® Laminated Filter Media LL–5211 A–A by Hollingsworth & Vose Company (1 page, undated).

*Primary Examiner*—Vivian Chen
(74) *Attorney, Agent, or Firm*—Ohlandt, Greeley, Ruggiero & Perle LLP; Shirley S. Ma

(57) ABSTRACT

A composite media comprising a backing sheet, a covering sheet, and a layer disposed between said backing sheet and said covering sheet, said layer having particles of active ingredient, binder particles, and stabilizing particles, wherein the active particles are coalesced by the binder particles, wherein each of the stabilizing particles bonds with both the backing sheet and the covering sheet, and wherein the stabilizing particles are larger than the binder particles.

20 Claims, 2 Drawing Sheets

U.S. PATENT DOCUMENTS

| | | | |
|---|---|---|---|
| 4,329,157 A | 5/1982 | Dobo et al. | 55/16 |
| 4,344,775 A | 8/1982 | Klein | 55/75 |
| 4,379,772 A | 4/1983 | Solomon et al. | 264/49 |
| 4,383,904 A | 5/1983 | Gestaut | 264/122 |
| 4,384,957 A | 5/1983 | Crowder et al. | 210/656 |
| 4,384,987 A | 5/1983 | Crowder | |
| 4,395,332 A | 7/1983 | Klein | 210/496 |
| 4,420,590 A | 12/1983 | Gartner | 525/357 |
| 4,488,969 A | 12/1984 | Hou | 210/679 |
| 4,512,897 A | 4/1985 | Crowder et al. | 210/656 |
| 4,535,004 A | 8/1985 | Haas et al. | 427/212 |
| 4,535,005 A | 8/1985 | Haas et al. | 427/212 |
| 4,547,195 A | 10/1985 | Jackson | 604/359 |
| 4,578,150 A | 3/1986 | Hou | 162/164.3 |
| 4,626,252 A | 12/1986 | Nishizawa et al. | 604/372 |
| 4,664,683 A | 5/1987 | Degen et al. | 55/387 |
| 4,664,812 A | 5/1987 | Klein | 210/679 |
| 4,665,050 A | 5/1987 | Degen et al. | 502/402 |
| 4,687,573 A | 8/1987 | Miller et al. | 210/143 |
| 4,692,161 A | 9/1987 | Puletti et al. | 604/366 |
| 4,743,373 A | 5/1988 | Rai et al. | 210/198.3 |
| 4,828,698 A | 5/1989 | Jewell et al. | |
| 4,872,870 A | 10/1989 | Jackson | 604/366 |
| 4,921,702 A * | 5/1990 | Banks et al. | 424/404 |
| 5,055,332 A | 10/1991 | Rhodes et al. | 428/74 |
| 5,114,582 A | 5/1992 | Sandstrom et al. | |
| 5,147,722 A | 9/1992 | Koslow | 428/402 |
| 5,151,301 A | 9/1992 | Kruger et al. | 427/294 |
| 5,225,242 A | 7/1993 | Frankosky et al. | 427/209 |
| 5,328,450 A | 7/1994 | Smith et al. | 604/366 |
| 5,342,333 A | 8/1994 | Tanzer et al. | 604/359 |
| 5,360,419 A | 11/1994 | Chen et al. | 604/374 |
| 5,413,747 A | 5/1995 | Akers et al. | 264/211 |
| 5,462,538 A | 10/1995 | Korpman | 604/366 |
| 5,672,419 A | 9/1997 | Mukaida et al. | 604/366 |
| 5,681,305 A | 10/1997 | Korpman | 604/359 |
| 5,792,513 A | 8/1998 | Koslow | 427/195 |
| 5,874,000 A | 2/1999 | Herding | 210/490 |
| 5,944,706 A | 8/1999 | Palumbo et al. | |
| 6,077,588 A * | 6/2000 | Koslow et al. | 428/114 |

* cited by examiner

METHOD OF STABILIZING COMPOSITE MEDIA AND MEDIA PRODUCED THEREBY

This application is a continuation-in-part of co-pending U.S. patent application No. 08/903,395, filed Jul. 22, 1997, U.S. Pat. No. 6,077, 588, which is a division of U.S. patent application Ser. No. 08/813,055, filed Mar. 7, 1997 and issued as U.S. Pat. No. 5,792,513.

FIELD OF THE INVENTION

The present invention relates generally to activated media. More particularly, the present invention relates to a method of stabilizing activated media and media produced thereby.

BACKGROUND OF THE INVENTION

It is often desirable to impregnate, cover, or otherwise treat a base material with an active or activated material, such as an absorbent or adsorbent material. One example would be a non-woven medium coated with agents having fluid adsorption and/or odor adsorption characteristics, as found in children's diapers, adult incontinence products, feminine hygiene products, and other adsorbent articles of clothing. Other examples include coated paper tissues and toweling, as well as surgical bandages and sanitary napkins. Other materials may be used as adsorbent materials, such as cyclodextrins or zeolites for odor control, or other adsorbents such as silicates, aluminas, or activated carbons.

The active, i.e., adsorbent, materials used to coat a base material may be fibrous or particulate materials. However, certain materials known in the art (e.g., fluff pulp fibers) have limited adsorption capacity, and hence perform disappointingly during normal wear. In addition, products containing such materials are often heavy and/or bulky. Thus, it is preferable to use at least some portion of particles composed of super adsorbent polymers (SAP).

Yet, it is difficult to immobilize powdered or small granular particles of SAP. Historically, microscopic active materials were immobilized on foams or on surfaces coated with a thin layer of pressure-sensitive adhesive. U.S. Pat. No. 5,462,538 to Korpman is an example of a method of immobilizing adsorbent material on a surface coated with a thin layer of pressure-sensitive adhesive. Using this method may produce large gaps between individual microscopic adsorbent elements. Also, the resulting adsorbent core has only a single layer of adsorbent material. PCT Publication No. WO 94/01069 to Palumbo is another example of a method of immobilizing particulate adsorbent material. However, the adsorbent particles are not bonded to the substrates. Moreover, the adsorbent particles are not in significant contact with the binder particles. Thus, neither method effectively restrains powdered or small granular particles of an active ingredient.

As a more effective alternative, U.S. Pat. No. 5,792,513, which is fully incorporated herein by reference, discloses a product formed from a composite mixture of adsorbent particles and binder particles fused to a substrate. While this product provides excellent absorption characteristics, the particles swell when exposed to fluid and then separate from the substrate and each other during normal use. This loose material is then free to slump or move.

In light of the foregoing, there remains a need for media, and a method of producing such media, in which the particles of an active ingredient are substantially immobilized even after they have become swollen, while maintaining excellent composite integrity.

SUMMARY OF THE INVENTION

The present invention provides an improved composite medium, in which the particles of an active ingredient are substantially immobilized. A further object is to provide absorbent or adsorbent articles having stabilizing particles dispersed throughout a coalesced composite layer of particles of an active ingredient and binder particles. By substantially immobilizing the particles of an active ingredient the present invention effectively prevents migration of the particles of an active ingredient, thereby creating an adsorbent product with enhanced integrity throughout the use cycle of the product.

Accordingly, the present invention provides composite media and a method of producing them. The composite media contain a coalesced composite mixture of particles of an active ingredient and binder particles. The binder particles preferably also fuse the composite structure to front and back substrates. The composite media also have stabilizing particles that fuse with both the particles of the active ingredient and the substrates, thereby forming a composite medium according to the present invention.

DETAILED DESCRIPTION OF THE INVENTION

Figure 1:
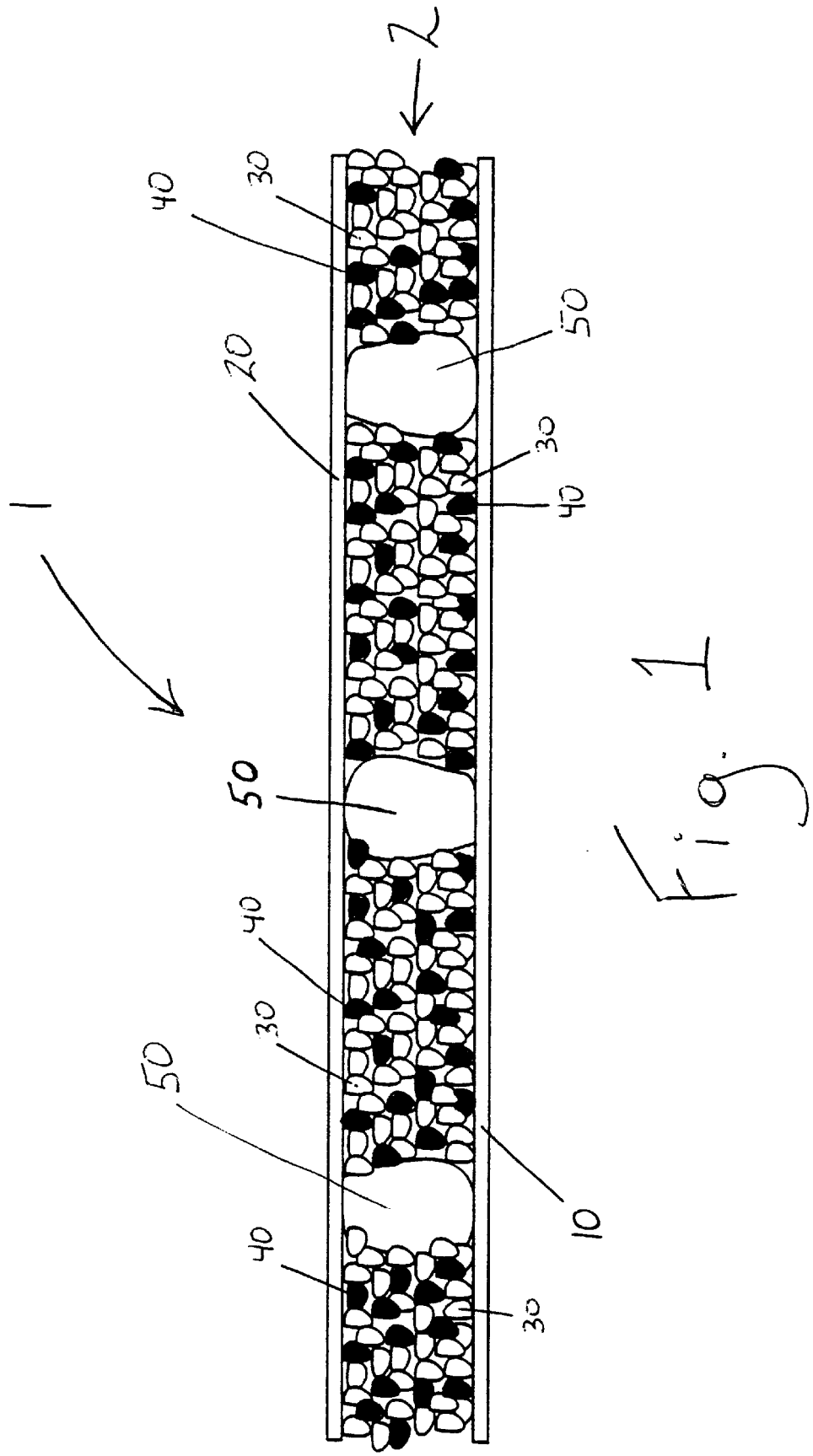
FIG. 1 is a side plan-view of the composite media of the present invention.

Referring to the drawings and, in particular, FIG. 1, there is provided a composite medium generally indicated as 1. Composite medium 1 has a backing substrate 10 and a covering substrate 20.

Backing substrate 10 and covering substrate 20 may be formed of various materials depending upon the application. By way of example, substrates 10, 20 may be a permeable material, such as a non-woven fibrous material, e.g., spunbonded polyester or polyolefin. Woven substrates may also be used. Furthermore, substrates 10, 20 may optionally be formed using cellulosic materials, such as paper, or a combination of cellulosic and thermoplastic fibers. Either substrate 10 or 20 may also be an impermeable material, such as a plastic film (e.g., Mylar®), a permeable backsheet or membrane or another suitable material.

The particular material selected for substrates 10, 20 can also effect the kinetics of adsorption of composite medium 1. For example, substrates 10, 20 can modify the mean pore size and the overall porosity, provide supplemental adsorption, improve tensile strength, flexibility, and pleatability, and effect wicking and fluid distribution.

Between substrates 10, 20, there is a layer, generally indicated as 2. Layer 2 has particles of an active ingredient 30, binder particles 40, and stabilizing particles 50. Particles of an active ingredient 30 are coalesced or fused together by binder particles 40. An amount of binder particles 40 may also be fused to points on either substrates 10 or 20, thereby also binding particles 30 to substrates 10 and 20. However, binding particles 40 will only be fused with one of substrates 10 and 20, rather than both. Stabilizing particles 50 may also be bonded to particles of an active ingredient 30 and, in contrast to binding particles 40, are fused to both backing substrate 10 and covering substrate 20, thereby forming a stabilizing bond or quilting effect.

In other words, as shown in FIG. 1, because of their smaller size, each binding particle 40 may bind to either substrate 10 or substrate 20, but not both, or to neither of substrates 10 and 20.

The thickness of layer 2 will vary depending on a variety of factors, including the size of the particles 30, 40, and 50, the quantity of particles 30, 40, and 50, the degree of coalescence between particles 30, 40, and 50, and whether other particles or fibers, such as fluff pulp, are used in layer 2. Preferably, the thickness of layer 2 is about 0.2 mm to about 5 mm.

Particles of an active ingredient 30 can potentially be formed of any material. For example, particles of an active ingredient 30 may absorb or adsorb fluids or gases. Furthermore, particles of an active ingredient 30 may be used to release fluids or gases held therein, for example, to deliver fluids, such as medicaments. Materials such as iodinated resin, activated carbon, activated alumina, aluminum powders, nickel powders, alumina-silicates, ferromagnetic materials, ion-exchange resins, manganese or iron oxides, zeolites, glass beads, ceramics, diatomaceous earth, and cellulosic materials can also be used as particles of an active ingredient 30. In addition, particles of an active ingredient 30 may also be polymeric materials, such as SAP. The cross sectional size of particles of an active ingredient 30 is preferably within a range of about 5 microns to about 5000 microns.

Materials forming binder particles 40 may potentially include any material known in the art. In particular, thermoplastic and thermoset materials are useful for the practice of the present invention. For example, binder particles 40 may be polyethers, polyolefins, polyvinyls, polyvinyl esters, polyvinyl ethers, ethylene-vinyl acetate copolymers, or a mixture thereof. Also, suitable binder particles may be produced from particulate thermoset resins known in the art, such as phenol-formaldehyde or melamine resins, with or without additional crosslinking agents. Preferably, binder particles 40 are present in such an amount and at such a size that they do not substantively interfere with the functioning of particles 30. Binder particles 40 are preferably about 5 microns to about 50 microns in size.

The critical feature of this invention resides in stabilizing particles 50 that are used to form through-web stabilizing bonds within layer 2. First, stabilizing particles 50 perform a similar function as binder particles 40, specifically coalescing or fusing together particles of an active ingredient 30. However, they are extremely limited in their capacity to stabilize the active ingredient particles because they are large and provide limited surface area to interface with the active ingredient and they are generally present in small amounts, again limiting their ability to stabilize other particles. Stabilizing particles 50 are also adhered or fused to both substrates 10, 20 because they are selected to have a particle size roughly equal to or greater than the thickness of layer 2. Materials forming stabilizing particles 50 are potentially any suitable material, such as the materials listed in reference to binding particles 40, e.g., a thermoplastic or a thermoset material. Stabilizing particles 50 are preferably present in such an amount and at such a size that they do not substantively interfere with the functioning of particles of an active ingredient 30 and binder particles 40. It is preferred that stabilizing particles 50 be both larger in size and fewer in number compared to binder particles 40. Preferably, stabilizing particles 50 are equal to or larger than the thickness of layer 2, so as to allow stabilizing particles 50 to span the entire thickness of layer 2 and directly adhere to substrates 10, 20. However, stabilizing particles may be smaller than the thickness of layer 2, for instance, if a ribbed effect for composite medium 1 is desired. In addition, stabilizing particles may be intimately grouped together, thereby binding to both substrates 10, 20 in the aggregate.

Figure 2:
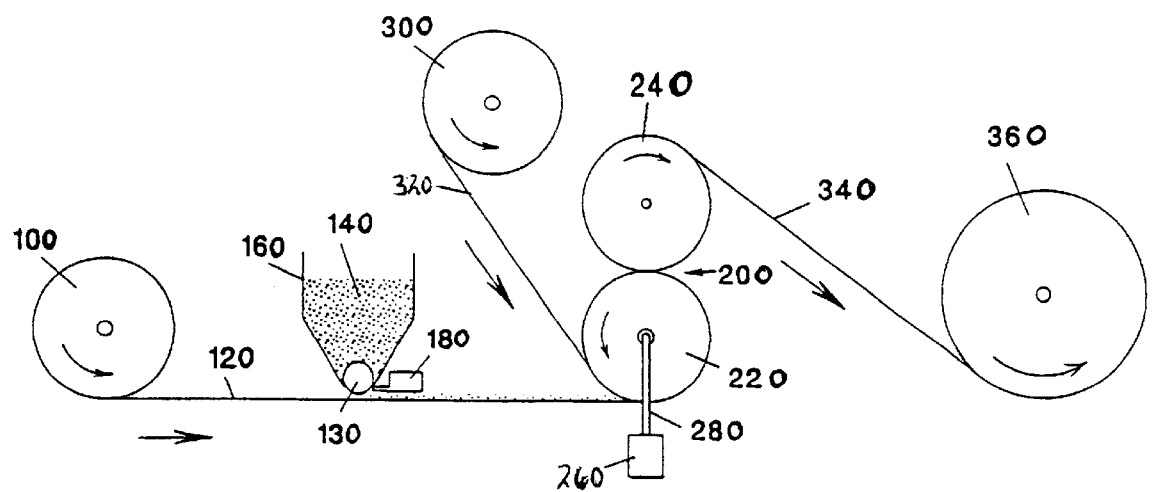
FIG. 2 is a schematic diagram illustrating an apparatus for the practice of the method of this invention.

FIG. 2 illustrates an exemplary apparatus for the practice of this invention. A supply roll 100 provides a substrate 120 to be treated, such as a nonwoven tissue or toweling paper. Downstream from supply roll 100 is a knurled roller 130 positioned to receive a mixture of particles of an active ingredient 30, binder particles 40, and stabilizing particles 50, the mixture generally being indicated as 140 and dispensed from a hopper 160. Mixture 140 is applied to the upper surface of substrate 120 as a continuous coating or, alternatively, as a coating of a specific design such as, for example, stripes. A brush 180 may be employed to aid in removing mixture 140 from knurled roller 130. Thereafter, substrate 120 is passed through a nip 200 between a heated idler roller 220 and a drive roller 240. Alternatively, before being passed through nip 200, substrate 120 may also be preheated, for example, by a convection or infrared oven. A pneumatic cylinder is connected via a rod 280 to the axle of idler roller 220 to maintain a desired pressure on substrate 120 within nip 200. In passing over the surface of heated roller 220, mixture 140 is heated to a temperature equal to or greater than the softening temperature of binder particles 40 and stabilizing particles 50, but lower than the softening temperature of particles of an active ingredient 30. Within nip 200, binder particles 40 and stabilizing particles 50 fuse under pressure with particles of an active ingredient 30, while stabilizing particles 50 also fuse with substrate 120. An amount of binder particles 40 may fuse with substrate 120. Furthermore, in a preferred alternative to the above described apparatus, a second supply roll 300 of a substrate 320, which may be of the same or a different material from that of substrate 120, is also passed between nip 200 on the top of mixture 140. Stabilizing particles 50 fuse with substrate 320 and an amount of binder particles 40 may also fuse with substrate 320. However, while stabilizing particles 50 fuse with both substrate 120 and 320, binder particles 40 will only fuse with either substrate 120 or 320. Upon leaving the nip 200, binder particles 40 and stabilizing particles 50 cool and harden. The composite medium 240 passes onto a takeup roll 360.

Coalescing particles of an active ingredient 30 with interposed binder particles 40 and stabilizing particles 50 results in more complete coverage of the backing substrate 10 and places particles of an active ingredient 30 in closer proximity to each other. In addition, it is possible to vary the depth and porosity of layer 2 and to have multiple layers of active ingredient fully stabilized by binder particles 40. When composite layer 1 contains SAP and is wetted, the SAP particles swell and generally break their bonds with binder particles 40 and any bonds that might exist with stabilizing particles 50. However, the bonds between substrates 10 and 20 and stabilizing particles 50 are retained and prevent the wholesale disassembly of composite layer 1. These stable bonds do not prevent local swelling of the composite layer 1, but do provide localized stabilization of composite layer 1 at each point where stabilizing particle 50 spans composite layer 1. These bonds provide a random quilting effect that prevents the movement of the swollen SAP mass.

Although composite medium 1, and the method of producing such a medium, has been described with respect to one or more particular embodiments, it will be understood that other embodiments of the present invention may be employed without departing from the spirit and scope of the present invention.

Hence, the present invention is deemed limited only by the appended claims and the reasonable interpretation thereof.

What is claimed is:

1. A composite medium comprising:

a backing sheet;

a covering sheet; and a layer disposed between said backing sheet and said covering sheet, said layer having particles of active ingredient, binder particles, and stabilizing particles, wherein said active particles are coalesced by said binder particles, and wherein each of said stabilizing particles forms a bond with both said backing sheet and said covering sheet, said stabilizing particles being of a size larger than said binder particles.

2. The composite medium of claim 1, wherein said backing sheet is an impermeable material.

3. The composite medium of claim 1, wherein said backing sheet is a permeable material.

4. The composite medium of claim 1, wherein said covering sheet is a permeable material.

5. The composite medium of claim 1, wherein said layer has an average thickness of about 0.2 mm to 5 mm.

6. The composite medium of claim 1, wherein said particles of an active ingredient are formed from at least one component selected from the group consisting one of: adsorbent particles, absorbent particles, particles that release liquid or gases held therein, and mixtures thereof.

7. The composite medium of claim 1, wherein said particles of an active ingredient are formed from at least one component selected from the group consisting one of: iodinated resin, activated carbon, activated alumina, alumina-silicates, ion-exchange resins, manganese oxides, iron oxides, zeolites, hydrophilic polymeric materials, and mixtures thereof.

8. The composite medium of claim 1, wherein said particles of an active ingredient have an average particle size of between about 5 microns to 5000 microns.

9. The composite medium of claim 1, wherein said binder particles are formed from at least one component selected from the group consisting one of thermoplastic materials, thermoset materials, and combinations thereof.

10. The composite medium of claim 1, wherein said binder particles are formed from at least one component selected from the group consisting of: polypropylene, linear low-density polyethylene, low density polyethylene, ethylene-vinyl acetate copolymer, polyolefin, phenol-formaldehyde resin, melamine resin, and mixtures thereof.

11. The composite medium of claim 1, wherein said binder particles have an average particle size of between about 5 microns to 50 microns.

12. The composite medium of claim 1, wherein said stabilizing particles are formed from at least one component selected from the group consisting of thermoplastic materials, thermoset materials, and combinations thereof.

13. The composite medium of claim 1, wherein said stabilizing particles are formed from at least one component selected from the group consisting of polypropylene, linear low-density polyethylene, low density polyethylene, ethylene-vinyl acetate copolymer, polyolefin, phenol-formaldehyde resin, melamine resin, and mixtures thereof.

14. The composite medium of claim 1, wherein said stabilizing particles have a particle size equal to or greater than the thickness of said layer.

15. The composite medium of claim 1, wherein said stabilizing particles are present in an amount and in a size so as to not interfere with the functioning of said active particles and said binder particles.

16. The composite medium of claim 1, wherein said stabilizing particles are fewer in number than said binder particles.

17. The composite medium of claim 1, wherein said stabilizing particles are smaller than the thickness of said layer.

18. The composite medium of claim 1, having regions wherein several stabilizing particles group together to bind the backing sheet and the covering sheet.

19. The composite medium of claim 1, wherein a portion of said binder particles also bind a portion of said active particles to at least one of said backing sheet and said covering sheet.

20. The composite medium of claim 1, wherein said particles of active ingredient comprise a super adsorbent polymer.

* * * * *